US00PP30156P2

(12) United States Plant Patent
Hogenboom

(10) Patent No.: US PP30,156 P2
(45) Date of Patent: Jan. 29, 2019

(54) ***PHLOX* PLANT NAMED 'HOG1702'**

(50) Latin Name: *Phlox paniculata*
Varietal Denomination: HOG1702

(71) Applicant: Hogenboom Phloxen, Roelofarendsveen (NL)

(72) Inventor: Jeroen Hogenboom, Roelofarendsveen (NL)

(73) Assignee: Hogenboom Phloxen, Roelofarendsveena (NL)

( * ) Notice: Subject to any disclaimer, the term of this patent is extended or adjusted under 35 U.S.C. 154(b) by 0 days.

(21) Appl. No.: 15/732,247

(22) Filed: Oct. 12, 2017

(51) Int. Cl.
*A01H 5/02* (2018.01)

(52) U.S. Cl.
USPC ..... Plt./320

(58) Field of Classification Search
USPC ..... Plt./263.1, 320
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

'HOG1702' is a new and distinctive variety of *Phlox* plant which is characterized by improved plant vigor, a spreading to upright growth habit, dark green elliptic to narrow ovate foliage, and an abundance of pink salverform flowers with a dark pink floral throat. The new variety propagates successfully by stem cuttings and has shown to be uniform and stable in the resulting generations from asexual propagation.

3 Drawing Sheets

Latin name of the genus and species: The Latin name of the genus and species of the novel variety disclosed herein is *Phlox paniculata.*

Variety denomination: The inventive variety of *Phlox* disclosed herein has been given the variety denomination 'HOG1702'.

BACKGROUND OF THE INVENTION

Parentage: 'HOG1702' is a seedling selection resulting from the controlled pollination of an emasculated *Phlox paniculata* 'Crissy' plant (not patented in the United States; Netherlands PBR application number VBL146), the seed parent, with *Phlox paniculata* 'Dynasty' (not patented), the pollen parent, at a commercial nursery in Roelofarendsveen, Netherlands, in June of 2010. Seed from said cross was harvested, then germinated, and the resulting seedlings were grown to a mature size in order to evaluate for desirable commercial characteristics. In approximately June of 2011, the inventor selected the new *Phlox* cultivar due to its improved plant vigor and light pink flowers with a dark pink floral throat. This new and distinctive cultivar was given the name 'HOG1702'.

Asexual Reproduction: Asexual reproduction of 'HOG1702' was first accomplished in August of 2011 by rooting softwood stem cuttings at a commercial greenhouse in Roelofarendsveen, Netherlands. Eight successive generations have shown that the unique features of the instant cultivar are stable and reproduce true to type.

SUMMARY OF THE INVENTION

The cultivar 'HOG1702' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Phlox* cultivar, 'HOG1702'.

1. *Phlox* 'HOG1702' exhibits improved plant vigor with good production and garden performance; and
2. *Phlox* 'HOG1702' exhibits a spreading to upright growth habit with a broad obovate form; and
3. *Phlox* 'HOG1702' exhibits dark green elliptic to narrow ovate foliage; and
4. *Phlox* 'HOG1702' exhibits an abundance of pink salverform flowers with a dark pink floral throat; and
5. *Phlox* 'HOG1702' exhibits flowers which, when cut, retain their color without fading.

BOTANICAL DESCRIPTION OF THE PLANT

Figure 1:
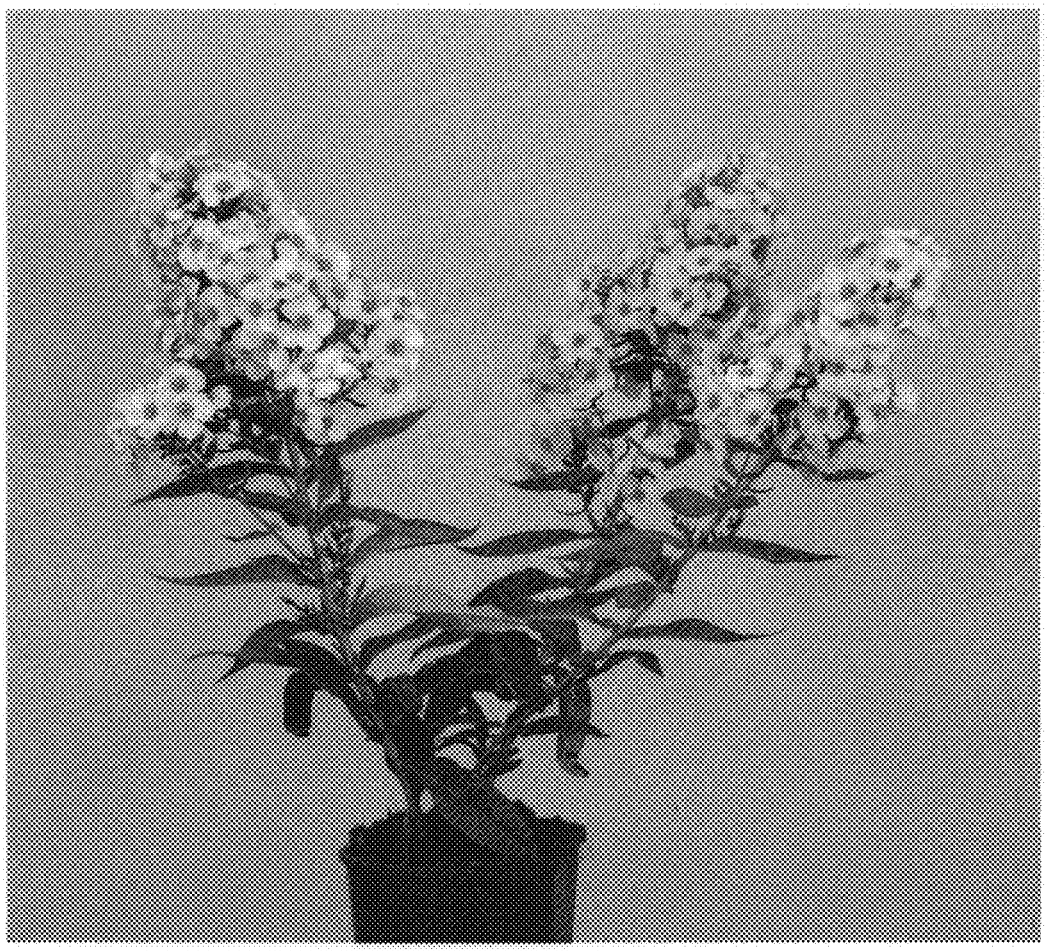
FIG. 1 shows, as nearly true as it is reasonably possible to make the same in color illustrations of this type, an exemplary 'HOG1702' plant at approximately 12 month old, potted into a 13 cm nursery container, grown outdoors in Roelofarendsveen, Netherlands.
Figure 2:
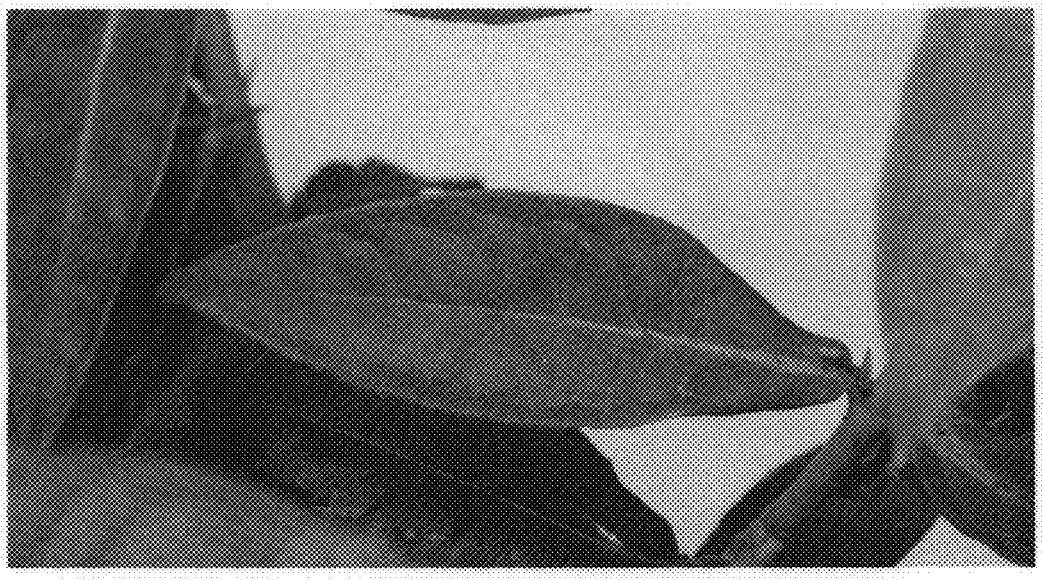
FIG. 2 shows, as nearly true as it is reasonably possible to make the same in color illustrations of this type, the typical foliage of the plant in FIG. 1.
Figure 3:
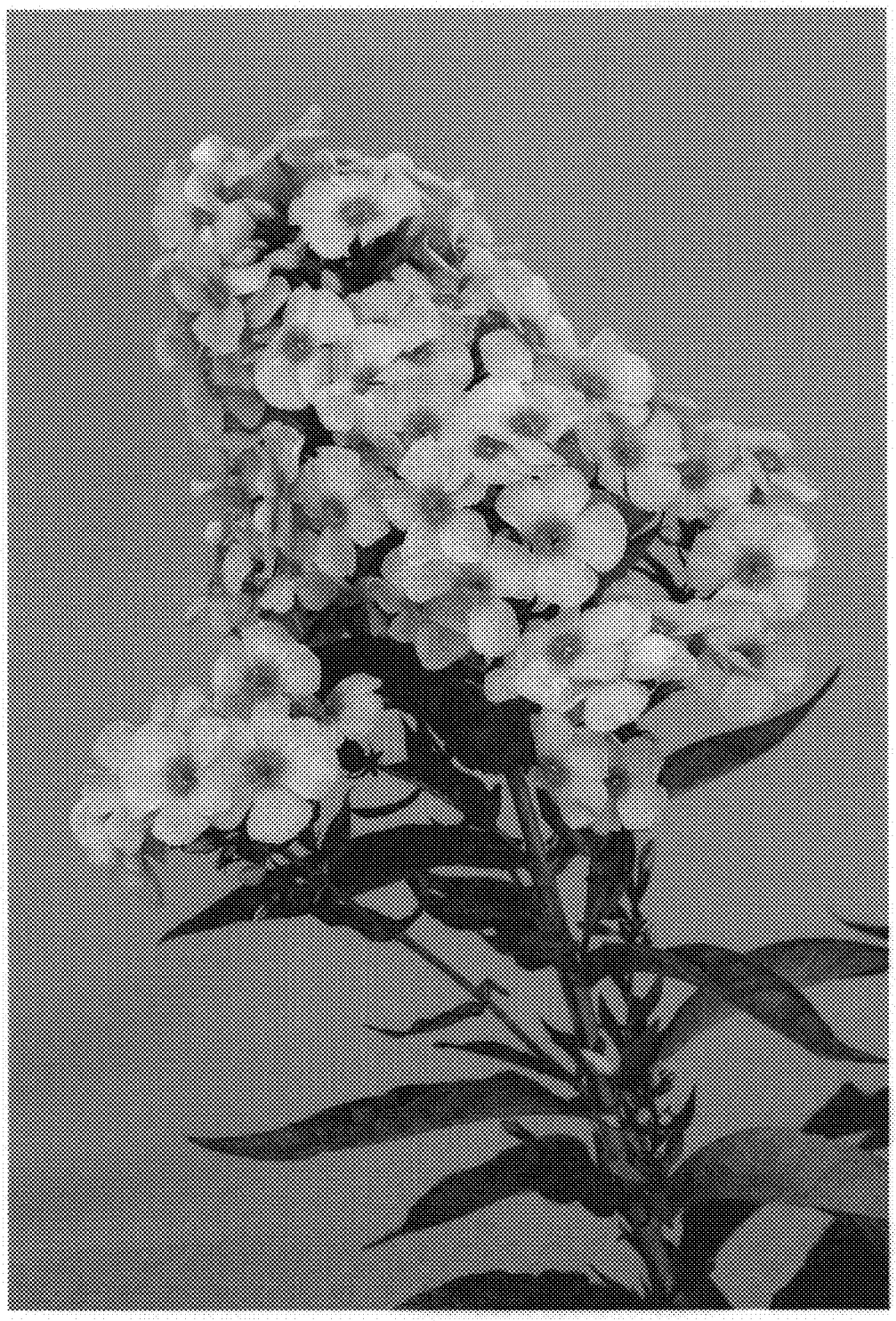
FIG. 3 shows, as nearly true as it is reasonably possible to make the same in color illustrations of this type, the typical inflorescence of the plant in FIG. 1.

The following observations and measurements were made in August of 2017 and describe averages from a sample set of six specimens of 12 month old 'HOG1702' plants grown in 13 cm nursery containers grown outdoors in Roelofarendsveen, Netherlands. Plants were produced using conventional field-grown production protocols for *Phlox* which consisted of regular fertilizer applications and natural rainfall, supplemented with drip irrigation as required. Pest or disease control measures were utilized in production as required. Plants were produced with full sun exposure and no photoperiodic treatments or artificial light was given to the plants.

Those skilled in the art will appreciate that certain characteristics will vary with older or, conversely, with younger plants. 'HOG1702' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'HOG1702' and a comparison with the parent plants and most similar variety of *Phlox* are provided below.

General plant description:

*Growth habit*.—Herbaceous perennial; spreading to upright.

*Plant form*.—Broad obovate.

*Average height*.—37.0 cm, from the soil level to the top of the foliar plane, and 48.4 to the top of the floral plane.

*Plant spread*.—Average of 61.9 cm.

*Growth rate*.—Moderate.

*Plant vigor*.—Moderate.

*Propagation type*.—Softwood stem cuttings.

*Time to initiate roots*.—Approximately 28 days to initiate roots at 20 degrees Celsius; 4 weeks to produce a fully rooted cutting.

*Time to produce a finished plant*.—Approximately 12 months are needed to produce a marketable plant in an 13 cm container.

*Pest resistance and susceptibility*.—Not any more or less tolerant or susceptible to pests or diseases known to effect *Phlox*.

*Temperature tolerances*.—USDA Zones 6 to 10; at least tolerant of temperatures ranging from minus 20 degrees Celsius to 35 degrees Celsius. Moderate tolerance to rain inundation; high tolerance to wind.

Root system:

*General*.—Moderately fibrous; freely branched; moderately dense.

*Distribution in the soil profile*.—Shallow.

*Diameter of primary roots*.—0.2 cm.

*Color*.—Yellow-white, nearest to a combination of RHS 158B and 158C.

*Texture*.—Smooth, with no root hairs.

Stem:

*Branching habit*.—Main stems with no lateral branching. Pinching isn't required but may improve branching.

*Number of main stems per plant*.—An average of 3 main stems.

*Number of lateral branches per plant*.—0.

*Appearance; cross-section*.—Rounded.

*Length of lateral branches*.—36.5 cm.

*Diameter of lateral branches*.—0.6 cm.

*Internode length on lateral branches*.—3.2 cm.

*Aspect*.—Approximately 45 degrees from vertical.

*Strength*.—Very strong.

*Color, juvenile*.—Yellow-green, nearest to RHS 144C.

*Color, mature*.—Yellow-green, nearest to in between RHS 144A and 144B.

*Color at internodes*.—Yellow-green, nearest to in between RHS 144A and 144B.

*Texture and luster*.—Glabrous, smooth and moderately glossy.

Foliage:

*Arrangement*.—Opposite.

*Attachment*.—Petiolate.

*Division*.—Simple.

*Quantity of leaves*.—24.

*Petioles*.—Length — 0.3 cm. Diameter — Petiole flattened; average width is 0.5 cm and average height is 0.3 cm high. Strength — Strong. Texture and luster, adaxial surface — Glabrous, smooth, and slightly glossy. Texture and luster, abaxial surface — Glabrous, smooth, and slightly glossy. Color, adaxial surface — Yellow-green, nearest to RHS 144C. Color, abaxial surface — Yellow-green, nearest to RHS 144C.

*Lamina*.—Dimensions — 12.0 cm long and 3.7 cm wide. Shape of blade — Elliptic to narrow ovate. Attitude — At an angle of approximately 30 degrees to the main stem. Aspect — Carinate; curled upward at the distal end. Apex — Apiculate. Base — Truncate. Margin — Entire but slightly rough to the touch due to microscopic serration; very slightly undulated. Pubescence, texture and luster of adaxial surface — Glabrous, slightly rugose, and very slightly glossy. Pubescence, texture and luster of abaxial surface — Glabrous, moderately rugose, and matte. Color — Juvenile foliage, adaxial surface — Green, nearest to RHS 143B, and heavily suffused with black, nearest to RHS 203A. Juvenile foliage, abaxial surface — Green, nearest to RHS 143C, and heavily suffused with brown, nearest to in between RHS 200A and 200B. Mature foliage, adaxial surface — Green, nearest to RHS NN137A. Mature foliage, abaxial surface — Yellow-green, nearest to RHS 147B. Venation — Pattern — Pinnate. Mature foliage venation, adaxial surface — Yellow-green, nearest to RHS 145A. Mature foliage venation, abaxial surface — Yellow-green, nearest to RHS 145A.

Inflorescence:

*Type*.—Panicle.

*Natural flowering season*.—Summer to late summer in Roelofarendsveen, Netherlands.

*Time to flower*.—Approximately 10 months.

*Dimensions*.—18.2 cm high, not including peduncle, and 17.7 cm in diameter.

*Abundance of inflorescence*.—Approximately 3 inflorescence per plant.

*Quantity of open flowers per plant*.—Approximately 360.

*Quantity of buds per plants*.—Approximately 300.

*Attitude*.—Upright.

*Peduncles*.—Length — Average of 12.8 cm. Diameter — Average of 0.35 cm. Strength — Very strong. Texture — Smooth; glabrous. Luster — Moderately glossy. Color — Yellow-green, nearest to RHS 144A.

Flower buds:

*Shape*.—Elliptic.

*Dimensions*.—1.4 cm long and 0.5 cm in diameter.

*Texture*.—Smooth; glabrous.

*Luster*.—Matte.

*Color*.—The distal half of the bud is pink, nearest to RHS NN47D, and the proximal half of the bud comprising the immature calyx is a combination of greyed-purple, nearest to RHS 187A, and purple, nearest to RHS N77D.

Flower:

*Flowering habit*.—Freely flowering.

*Shape*.—Salverform.

*Flower depth*.—3.0 cm.

*Flower diameter*.—3.8 cm.

*Diameter of floral throat*.—0.4 cm.

*Floral throat texture*.—Glabrous; moderately velvety.

*Diameter of floral tube*.—0.3 cm.

*Length of floral tube*.—2.4 cm.

*Floral tube texture*.—Moderately covered with soft, very short hairs; hairs with an average length of 0.04 cm and colored green-white, nearest to RHS 1576D.

*Aspect*.—Flowers are upward and outward facing.

*Fragrance*.—Moderately to strongly fragrant; sweet and very pleasant, typical of *Phlox paniculata*.

*Lastingness*.—Approximately 10 days.

*Persistent*.—Self-cleaning.

*Pedicels*.—Dimensions — 0.4 cm long and 0.1 cm in diameter. Attitude — At an average angle of 60 degrees to the peduncle. Strength — Medium. Texture — Moderately covered with very short hairs; hairs with an average length of 0.02 cm and colored white; hairs are so minute that it is impossible to assign an R.H.S. color designation. Luster — Moderately glossy. Color — Yellow-green, nearest to RHS 146A.

*Petals*.—Quantity of Petals — 5. Arrangement — Single whorl; petals are rotate and fused into an elongated tube at the base; lower 58.5 percent of the petals are fused; free portion of the petals are slightly overlapping. Shape of petal lobes — Spatulate. Dimensions, free portion of petals — 4.1 cm long and 1.7 cm wide. Apex — Obtuse. Base — Fused into a tube. Margin — Entire; lightly undulated. Aspect — Cupped. Pubescence, texture and luster of upper surface — Glabrous, velvety and matte. Pubescence, texture and luster of lower surface — Glabrous, velvety and very slightly glossy. Petal lobe color when opening, upper surface — Nearest to in between red-purple, RHS 68D, and purple, RHS 75B; heavily suffused with darker red-purple towards the throat, nearest to RHS N74A. Petal lobe color when opening, lower surface — Purple, nearest to RHS 75C. Petal lobe color when fully opened, upper surface — Purple, nearest to RHS 75B, and heavily suffused with darker red-purple towards the throat, nearest to RHS N74A; not fading. Petal lobe color when fully opened, lower surface — Purple, nearest to a combination of RHS 75B to 75D; not fading. Petal venation when fully opened, upper surface — Purple, nearest to RHS 75B, and heavily suffused with darker red-purple towards the throat, nearest to RHS N74A. Petal venation when fully opened, lower surface — Purple, nearest to a combination of RHS 75B to 75D. Floral throat color — Red-purple, nearest to RHS N74C. Floral throat venation color — Red-purple, nearest to RHS N74C. Floral tube color, when fully opened — Red-purple, nearest to RHS 70A. Floral tube venation color — Red-purple, nearest to RHS 70A.

*Calyx*.—Shape — Rotate. Dimensions — 1.1 cm in diameter and 0.3 cm tall. Sepals — Arrangement — Rotate; lower 17.5% is fused. Quantity — 5. Shape — Lanceolate. Sepal dimensions — 1.1 cm long and 0.2 cm wide. Apex — Narrow apiculate. Base — Cuneate. Margin — Entire; not undulated. Texture and luster, upper surface — Glabrous, smooth, and slightly glossy. Texture and luster, lower surface — Glabrous, smooth, and slightly glossy. Color when opening, upper surface — Yellow-green, nearest to RHS 147B, and margined purple, nearest to RHS N77D. Color when opening, lower surface — Greyed-purple, nearest to RHS 187A, and margined purple, nearest to RHS N77D. Color when fully opened, upper surface — Yellow-green, nearest to a combination of RHS 144A and 144B, and lightly suffused with brown towards the apex, nearest to RHS 200B; margined purple, nearest to RHS 76D. Color when fully opened, lower surface — Green, nearest to RHS 138D, and heavily suffused with brown towards the apex, nearest to RHS 200A; margined purple, nearest to RHS 76D. Sepal venation when fully opened, upper surface — Yellow-green, nearest to a combination of RHS 144A and 144B, and lightly suffused with brown towards the apex, nearest to RHS 200B; margined purple, nearest to RHS 76D. Sepal venation when fully opened, lower surface — Green, nearest to RHS 138D, and heavily suffused with brown towards the apex, nearest to RHS 200A; margined purple, nearest to RHS 76D.

Reproductive organs:

*Androecium*.—Stamen quantity — 5. Filament length — 0.1 cm. Filament color — White, nearest to in between RHS 155A and 155B. Anther shape — Narrow oblong. Anther length — 0.25 cm. Anther width — 0.1 cm. Anther color — White, nearest to RHS 155A. Pollen, presence — Moderately abundant. Pollen, color — Greyed-yellow, nearest to RHS 160D.

*Gynoecium*.—Pistil quantity — 1. Pistil length — 2.1 cm. Style length — 2.0 cm. Style color — Yellow-green, nearest to RHS 145C. Stigma shape — Cleft; three-parted. Stigma length — 0.1 cm. Stigma diameter — 0.15 cm. Stigma color — Yellow-green, nearest to RHS 145C. Ovary color — Green, nearest to RHS 143B.

Seed and fruit: None observed.

COMPARISONS WITH THE PARENT PLANTS AND MOST SIMILAR VARIETY OF COMMON KNOWLEDGE

Plants of the new cultivar 'HOG1702' differ from its seed parent, *Phlox paniculata* 'Crissy' plant (not patented in the United States; Netherlands PBR grant number 33669), by the characteristics described in Chart 1.

CHART 1

| Characteristic | 'H0G1702' | 'Crissy' |
|---|---|---|
| General coloration of the flower. | Pink. | Purple. |

Plants of the new cultivar 'HOG1702' differ from its pollen parent, *Phlox paniculata* 'Dynasty' (not patented in the United States; Netherlands PBR grant number 35177), by the characteristics described in Chart 2.

CHART 2

| Characteristic | 'HOG1702' | 'Dynasty' |
|---|---|---|
| Leaf shape. | Leaves are more elliptic. | Leaves are more ovate. |
| Leaf length. | Shorter than 'Dynasty'. | Longer than 'HOG1702'. |
| Leaf thickness. | Thicker. | Thinner. |

Plants of the new cultivar 'HOG1702' may be distinguished from its most similar known commercial comparator, *Phlox* 'Bright Eyes' (not patented), by the characteristics described in Chart 3.

CHART 3

| Characteristic | 'H0G1702' | 'Bright Eyes' |
|---|---|---|
| Length of main stems. | Longer than 'Bright Eyes'. | Shorter than 'HOG1702'. |
| General coloration of mature foliage. | Darker green than 'Bright Eyes'. | Lighter green than 'HOG1702'. |
| Leaf shape. | Leaves are more elliptic. | Leaves are more ovate. Lighter pink. |
| General coloration of the flower. | Darker pink. | |

That which is claimed is:

1. A new and distinct variety of *Phlox paniculata* plant named 'HOG1702', substantially as described and illustrated herein.

* * * * *